United States Patent [19]

Dick et al.

[11] 4,150,109

[45] Apr. 17, 1979

[54] DEVICES FOR PROTECTING ANIMALS FROM ECTOPARASITES

[76] Inventors: Pierre R. Dick, 95 Avenue de la Lanterne; Max Rombi, 67 rue Rossini, both of 06 Nice, France

[21] Appl. No.: 857,685

[22] Filed: Dec. 5, 1977

Related U.S. Application Data

[63] Continuation of Ser. No. 673,994, Apr. 5, 1976, abandoned, which is a continuation-in-part of Ser. No. 572,296, Apr. 28, 1975, abandoned.

[30] Foreign Application Priority Data

May 7, 1974 [FR] France .................................. 74 15742
Apr. 16, 1975 [FR] France .................................. 75 11813

[51] Int. Cl.² .................... A01K 27/00; A01K 29/00; A01M 1/20
[52] U.S. Cl. ..................................... 424/28; 119/106; 119/156; 119/159; 424/14; 424/16; 424/78; 424/200; 424/219
[58] Field of Search ......................... 43/124, 131, 145; 119/106, 156, 159; 424/14, 16, 28, 78, 200, 219

[56] References Cited

U.S. PATENT DOCUMENTS

| 2,754,243 | 7/1956 | Gysin et al. | 424/200 |
| 3,852,416 | 12/1974 | Grubb et al. | 424/14 |
| 3,904,746 | 9/1975 | Aries | 424/28 |

FOREIGN PATENT DOCUMENTS

1568198  5/1969 France.

OTHER PUBLICATIONS

Chem. Abstr., 70#54086n (1970), of Fr. 1,568,198, Tamogan, Ltd. (Kleinberger et al.).
Chem. Abstr., 77#44283p (1972), Nelson et al., "Laboratory Release Rate Studies of Diazinon and Supracide from Poly(Vinyl Chloride) Formulations".
Chem. Abstr., 59#9255f (1963), Smittle et al., "Organophosphorus Insecticides for Control of Brown Dog Ticks Infesting Homes".
Chem. Abstr., 58#10676g (1963), Price et al., "A Practical Study of Brown Dog Tick Control".

*Primary Examiner*—Shep K. Rose
*Attorney, Agent, or Firm*—Cushman, Darby & Cushman

[57] ABSTRACT

Device for protecting animals from Ectoparasites comprising an active element

Insecticidal arrangement intended to be fastened to the neck of an animal, comprising an active element consisting of an active principle chosen from diazinone, diazoxone and the mixtures thereof, a solid macromolecular substance chosen from the vinyl and vinylidene substances, and a plasticizer, and an attachment member supporting said active member.

2 Claims, No Drawings

DEVICES FOR PROTECTING ANIMALS FROM ECTOPARASITES

This is a continuation, of application Ser. No. 673,994, filed Apr. 5, 1976 now abandoned, which in turn is a continuation-in-part application of Ser. No. 572,296, filed Apr. 28, 1975 (now abandoned).

The present invention relates to new arrangements which may be used round the necks of domestic animals and which are intended to protect the latter from ectoparasites, said arrangement consisting of a composition containing a plasticised vinyl polymer and diazinone or, preferably, diazoxone as insecticidal substance.

From French patent No. 1568198 by TAMOGAN Limited, compositions are known which contain a plasticised polymer and an insecticidal substance, such as DDVP, DIPTEREX and BROMEX, which can be used on parasitic insects; it is well known that DDVP works by releasing vapours. It is also known that DIPTEREX AND BROMEX are only slightly different from DDVP in their structure and that they work by giving off DDVP vapours arising from their decomposition.

The Applicants have now found that arrangements which were effective against parasitic insects on animals could work, not by their vapour, but by simple contact during the migratory movement of the parasites between the head and the other parts of the body of the host animal.

The Applicants have also found that diethyl O-(2-isopropyl-4-methyl-6-pyrimidinyl) thionophosphate, known under the name of Diazinone, and preferably diethyl O-(2-isopropyl-4-methyl-6-pyrimidinyl) phosphate, called diazoxone were particularly suitable for producing arrangements of this kind.

Compositions containing diazinone and plasticised polymer have also been described in said patent of Tamogan Limited, but these compositions consist solely of granules and it is neither stated nor suggested in said patent that such compositions could be used for providing an arrangement for use round the neck of a domestic animal.

The present invention therefore relates to an insecticidal arrangement intended to be fastened to the neck of an animal and containing the following elements:

A—diazinone and/or diazoxone as active principle,
B—a solid, macromolecular vinyl or vinylidene substance,
C—a plasticiser,
D—optionally, a dye, a pigment, a stabiliser and a deodorant,
E—optionally, a receptacle containing the rest of the insecticidal arrangement and consisting of a hollow section made of flexible plastic, which is insoluble in the active principle, which in turn has no, or virtually no solvent effect on the section, said section being sealed at its ends and having orifices all along its length, which is between 12 and 60 centimetres, and said receptacle being capable of carrying an attaching device,
F—optionally, a container, serving as case, which is impervious to the active principle.

The arrangements thus produced have, in comparison with those known which are based on DDVP, a much lower toxicity, owing to the fact that diazinone is five times less toxic than DDVP and, above all, because diazinone gives off virtually no toxic vapours, unlike DDVP, the latter having a vapour pressure over 100 times greater than that of diazinone. Diazoxone is even less toxic than diazinone. The $LD_{50}$ in the rat is 1600 mg/kg for diazoxone, whereas it is 450 mg/kg for diazinone.

Another advantage of the arrangements according to the invention lies in the much greater stability of diazinone and/or diazoxone compared with that of DDVP, particularly in the presence of humidity. The animal may go out in the rain or bathe without detriment to the arrangement, which is not the case with arrangements based on DDVP.

Another advantage lies in the very clean appearance of said arrangements, unlike those based on DDVP which are always viscous and unpleasantly oily to the touch.

Another advantage lies in the excellent effectiveness of the arrangements based on diazinone and/or diazoxone, which is clearly superior to that which can be obtained with those based on DDVP, Tetrachlorvinphos or Forpirate.

After an arrangement according to the invention, using diazoxone, has been moulded or extruded, the arrangement has virtually no unpleasant smell. Moreover, diazoxone is more active than diazinone.

The quantity of active principle present in the arrangement is preferably between 1 and 30% and, better still, between 5 and 20% by weight, that of the macromolecular substance between 30 and 80%, preferably 40 to 60%, and that of the plasticiser from 10 to 50%, preferably 20 to 35%.

The macromolecular substance preferably has a weight of more than 1000; it is selected from the homopolymers and copolymers obtained starting from vinyl chloride, vinyl acetate, vinyl acetals, vinylalcohol, vinylbenzene and divinylbenzene and vinylidene chloride; the copolymers may, in addition, contain additional components such as ethylenic, propylenic, butadienic, isoprenic, acrylic and methacrylic components.

Preferably, the macromolecular substance is a polymer or copolymer of a vinyl compound such as, for example, the polyvinyl halides. The particularly preferred macromolecular substances are polymers or copolymers of vinyl chloride.

The macromolecular substance preferably contains one or more plasticisers.

The plasticisers are liquid esters with a vapour pressure of less than 0.0001 mm/Hg at 25° C. Some nonrestrictive examples of plasticisers are: diethyl, dimethyl, dipropyl, dibutyl, dihexyl, dioctyl and didecyl phthalate, dibutyl, diamyl, dinonyl, dioctyl, and didecyl adipate, dipropyl, dibutyl, dibenzyl and dioctyl sebacate, diethyl, dipropyl and dibutyl citrate, triphenyl and tricresyl phosphate and the triglycerides.

The preferred plasticisers are dibutyl phthalate and dioctyl adipate, which make it possible to obtain an arrangement with good flexibility, on the surface of which the active principle appears rapidly and regularly.

Suitable stabilisers are all those known from diazinone, of which the following can be mentioned: epoxides such as epichlorohydrin, calcium, magnesium or potassium stearate, the laurates and palmitates of these same metals, chlorinated terphenyls and butoxy-propylene-glycol. The preferred stabilisers are calcium or magnesium stearate and epoxidised soya bean oil.

Suitable deodorants are all those which are capable of masking the smell of diazinone and the impurities it contains and which are acceptable to domestic animals. Examples of these are conmarine and vanilline.

The hollow section, if used, is preferably made from polyethylene, polypropylene or polyamide; its shape in cross section is not critical. It may be, for example, circular, elliptical, semicircular, lenticular, square or rectangular; its internal diameter is calculated with reference to the band it must hold and is therefore slightly greater than the thickness of the latter; the thickness of the walls of the section is preferably between 0.5 and 3 mm; forms and dimensions of this kind are easily obtained by extrusion.

The ends of the section are closed, for example, by welding or by one or more rivets.

The orifices preferably represent, in all, a total open surface of such a size that the ratio of the latter, expressed in $cm^2$, to the weight of the insecticidal composition, expressed in grams, is between 0.5 and 1.

The shape of the orifices is not cricial; they may be circular, square, rectangular, lozenge-shaped, star-shaped or any other desired shape.

The orifices are preferably distributed over not more than half the circumference of the hollow section, in order to prevent the active composition from coming into contact with the neck of the animal.

The attachment device may consist of a buckle fastened to one end of the section, the other end having a flat, flexible band, fitting the buckle, perforated or not, depending on the type of buckle, and made of leather or a plastic of the same kind as that of the section. The two ends of the section may also each have a buckle element which permit the section to be closed by joining the two elements.

The attachment device may also be a collection of hooks distributed along the section, allowing the latter to be attached to the usual collar of the animal to be protected.

The invention also related to processes for producing said arrangements. According to one of these processes, the constituents A, B, C and D are thoroughly mixed and the mixture is heated to 120° C. for 30 minutes in a preferably sealed container, in order to obtain a powder, which is optionally passed through a mill. This powder is used to form the arrangement desired, either by extrusion of by moulding in a material known to the specialists. The operation is carried out at a temperature preferably between 160 and 200° C.

According to another preparation process, the desired article is obtained directly, in the desired form and of the required dimensions, housed in its casing. According to this process, a solid material, with the desired form, consisting of macromolecular substance B, preferably plasticised, and an active liquid containing active principle A, and optionally a plasticiser and deodorant D, is placed inside a container F which serves as the casing, and which is impervious to the active liquid, and the volume of which is adapted so that the active liquid is in contact with at least part of the surface of material B; then the container is sealed in air-tight manner and the whole is stored at a temperature between 20° and 80° C. for a period, which is in inverse proportion to the temperature, of at least one day.

During storage, the active liquid passes, without any external intervention, into the solid material, wherein it is uniformly distributed by absorption.

The active liquid may contain, apart from the active principle and the optional constituents C and D, a solvent chosen from the succinic and maleic esters, such as the propyl, butyl, pentyl, hexyl, heptyl, octyl and decyl esters.

Material B may be prepared according to all the known methods of using and shaping plastics, such as injection moulding, pouring it on to a continuous belt, extrusion through a flat or annular draw-plate, calendering, drawing by dry or humid extrusion, followed by weaving or agglomeration.

In the techniques which use moulding, the solid material B is generally obtained directly in its final form and dimensions.

In the other techniques, a half-finished product is obtained, which is then shaped by cutting, sawing, forming, stamping, gluing, welding, etc.

The solid material may have any form, but it must give a ratio of surface available for contact with the active liquid/volume of at least 2 in the CGS system. The preferred shapes are plates, sheets, strips, tubes, sectioned rods, and, of these, particularly the forms of plates, tubes and strips may be used on a domestic animal.

Various structures may be used; the solid material B is, depending on the particular case: fibrous, alveolar, porous, spongy, foliated, felted or woven, but preferably compact or hollow. In the case of a compact mass, the ratio impregnation surface/volume may be increased by a non-smooth surface condition, such as undulating, grained, perforated or striated.

The form and the nature of the container are not critical, but it is necessary for it to be adapted so that the active liquid is in contact with at least part of the surface of material B, sufficient to permit, after the storage period, homogeneous penetration by the active liquid and uniform distribution of it in the material B; the container should be of such dimensions that all the material B and the active liquid can be held therein. It is desirable that the solid material B be totally bathed in the active liquid for most of the impregnation period. To satisfy this last condition, the container is preferably a small flexible bag, similar in form to the solid material B. The weight of active liquid to be absorbed according to the process is in the proportion of 0.1 to 2 parts of liquid to one part of B; when a solid material B is used which is in the form of a plate, sheet, strip of sectioned rod, this proportion is preferably between 0.2 to 1 part of liquid to one part of B; when a solid material B is used which is foliated, fibrous, felted or woven in structure, this proportion is preferably between 0.4 and 1.5 parts of liquid to one part of B; when a solid material B is used which is cellular or spongy in structure, this proportion is preferably between 1 and 2 parts of liquid to one part of B.

The order of introducing the solid mass and the active liquid into the container does not affect the impregnation mechanism, but it has been found that is was more practical to introduce the solid material first.

The container is given its air-tight seal by one of the methods which are well known in the packaging industry, such as, for example, corking, welding, glueing, crimping. The preferred method is welding. Depending on the nature of the casing material, welding is effected by direct thermal transfer, infra-red radiation or high-frequency current. According to a variant, the air-tight seal of the container is made after a vacuum has been created on the inside. The container thus emptied of air generally eliminated the risk of the arrangement exuding during storage. The container may also be emptied of air before sealing, on the condition that no air is allowed to go back in during sealing.

The minimum storage time for impregnating the solid material with all the active liquid depends on the nature and structure of the solid material B and the nature of the active liquid. Moreover, the minimum storage time decreases when the ratio surface/volume of solid material increases, when the weight ratio of solid/liquid increases, or when the temperature is increased.

The temperature at which storage takes place is preferably between +20 and +60° C.

The minimum time needed for impregnation is between 3 and 30 days.

A particularly interesting variant of the general process consists in using a solid material comprising a central cavity into which the active liquid to be absorbed is introduced.

This variant prevents direct contact between the liquid and the walls of the container and allows a greater rate of impregnation. According to this variant, the solid material B is flexible. Preferably, material B is made in the form of a flat bag or a tube with internal and external elliptical or, preferably, lenticular section. In the case of a tube with a lenticular section, one end is sealed by welding; the active liquid is introduced into it, then the other end is sealed by welding, letting as little air as possible into the tube. The whole is then placed in an air-tight container and stored as in the general case of the process. After total impregnation, the material B noticeably takes the form of a small flat strip. In this variant, the preferred embodiments use a material B in the form of tubes with a lenticular section, the dimensions of which are as follows: width (flattened tube) 1.5 to 6 cm, length 10 to 60 cm, thickness of the walls 1 to 5 mm.

In order to realise a variant of this kind, preferably a container is used which consists of a multilayer plastic sheet of the type known in the packaging field under the name "complex".

EXAMPLES 1 to 4

Insecticidal collars for large or medium-sized dogs
A-Composition

| A-Composition | |
|---|---|
| 1. diazinone | 12% |
| dibutyl phthalate | 22% |
| calcium stearate | 2% |
| epoxidised soya bean oil | 4% |
| polyvinyl chloride | 60% |
| 2. diazinone | 15% |
| dioctyl adipate | 20% |
| magnesium stearate | 2% |
| epoxidised soya bean oil | 3% |
| red pigment | 1% |
| conmarine | 1% |
| polyvinyl chloride | 58% |
| 3. diazinone | 20% |
| dipropyl phthalate | 10% |
| diheptyl adipate | 10% |
| calcium laurate | 1% |
| cyclohexene oxide | 2% |
| white pigment | 0.4% |
| green pigment | 0.6% |
| copolymer of vinylidene chloride/vinyl chloride (1:3) | 56% |
| 4. diazinone | 10% |
| dibutyl sebacate | 5% |
| diheptyl adipate | 25% |
| polyvinyl chloride | 60% |

B-PRESENTATION

The mixture obtained is poured hot (180° C. approximately) on to a cold surface to be cut into thin strips, or is extruded to the desired form and dimensions. An attachment device is fixed on, either by welding of using hooks or rivets. The thin strip may also be placed in a hollow section, as stated above. The length of the collar thus produced is adjusted to fit the neck of the animal for which it is intended; it is also possible to make it only in a large size which is then adapted to fit the animal, by cutting and removing the superfluous part. The arrangement may also be made as a hollow band into which a ribbon or a strip of leather provided with an attachment device is passed; the hollow band is obtained by extrusion or by combining two flat, thin bands by welding or stitching; in the latter case, one of the two bands, for example the one intended to face the animal's neck, may be an inert material such as canvas, leather, or a polymer such as those given for the hollow sectioned case.

Over a period of six months, tests were performed on dogs of various sizes, with a simple band (without a case) according to the compositions A-1, comparing it with bands bases on commercial DDVP (10% plasticised polyvinyl chloride). The effectiveness on fleas is summarised in the following table:

| Time from first use | DDVP collars | Collar A-1 |
|---|---|---|
| 1 month | 85% | 100% |
| 2 months | 63% | 99% |
| 3 months | 20% | 92% |
| 4 months | 11% | 88% |
| 5 months | 8% | 77% |
| 6 months | 5% | 61% |

Similarly, very high effectiveness on ticks was also noted (total mortality 8 to 12 hours after fitting the collar) for more than 4 months for the A-1 collars, whereas the activity disappeared around the middle of the second month in the case of the DDVP collars.

A flee re-infestation test was carried out twenty weeks after the A-1 collars were fitted; elimination of fleas in a proportion of 72 to 91% was observed in the twenty-four hours that followed.

An analysis of several collars, made after 3 months, showed that the A-1 collars still retained nearly 65% of their active principle, whereas the DDVP collars had not more than 20 to 25% of this active substance.

EXAMPLES 5 to 7

Collars for cats and small dogs

| A-Composition | |
|---|---|
| 5. diazinone | 10% |
| dibutyl phthalate | 23% |
| calcium palmitate | 2% |
| butyl epoxystearate | 3% |
| yellow pigment | 1% |
| polyvinyl chloride | 61% |
| 6. diazinone | 8% |
| dihexyl phthalate | 10% |
| dihexyl adipate | 18% |
| octyl epoxystearate | 2% |
| potassium stearate | 1% |
| orange pigment | 1% |
| polyvinyl acetate | 20% |
| polyvinyl chloride | 40% |
| 7. diazinone | 5% |
| dibutyl phthalate | 15% |

-continued

| | |
|---|---|
| dioctyl adipate | 15% |
| epoxidised soya bean oil | 1% |
| magnesium stearate | 1% |
| blue pigment | 0.3% |
| white pigment | 0.7% |
| copolymer ethylene/vinyl chloride (1:4) | 62% |

B-PRESENTATION

The process is the same as in the preceding cases, but using smaller dimensions.

EXAMPLE 8

A flexible strip of polyvinyl chloride was used, pigmented with green, and plasticised with dibutyl phthalate (30% of the material plasticised). This strip measured 30 cm in length by 15 mm in width and 6 mm thick, and weighes 28 grams.

The strip had a buckle at one end and the other was perforated with small holes a centimetre apart, over a length of 10 centimetres. This strip was introduced into a small bag sealed by welding, consisting of a sheet containing of 30 micron layer of polyethylene and a 25 micron layer of aluminum turned to the outside. The internal dimensions of the bag were 32×3 cm. Into the bag were poured 14 g of active liquid with the following composition:

| | |
|---|---|
| diazinone | 4.2 g |
| dibutyl succinate | 5.8 g |
| dibutyl phthalate | 4.0 g |

The bag was sealed by welding, creating a vacuum inside, and was stored for 15 days at 40° C. After this period, the bag was opened. It was noted that no free liquid remained in the bag. The strip weighed about 42 g and analysis showed that it contained just over 9.7% of diazinone, i.e. 4.1 g. This strip was suspended at a temperature of 22±2° C. and was wiped every two days with a non-woven cloth, new each time, which was then analysed. This operation showed that the quantity of active substance present in the active liquid, migrating to the surface, was, on average, between 17 and 18 mg/day and was still equal to 14.3 mg/day after four months of use.

EXAMPLES 9 and 10

Collars for cats and small dogs

| A9-Composition of the collar based on Diazoxone | |
|---|---|
| Diazoxone | 10% |
| dibutyl phosphate | 24% |
| calcium stearate | 2% |
| epoxidised soya bean oil | 3% |
| pigment and perfume | 1% |
| polyvinyl chloride | 60% |

| B10-Composition of the collar based on Diazinone | |
|---|---|
| diazinone | 10% |
| dibutyl phosphate | 24% |
| calcium stearate | 2% |
| epoxidised soya bean oil | 3% |
| pigment and perfume | 1% |
| polyvinyl chloride | 60% |

C-PRODUCTION

The two mixtures thus obtained are heated, then extruded or moulded under the same conditions, to the desired dimensions.

Over a period of 5 months, tests were carried out with the two arrangements, on dogs infested with fleas and ticks, and subjected to artificial re-infestation every week.

EFFECTIVENESS ON FLEAS

The comparative effectiveness of the two arrangements on fleas is summarised in the following table.

| time since first use | % fleas killed with collar A9 after 24 hours | time taken by arrangement A9 to kill all the fleas | % fleas killed with collar B10 after 24 hours | time taken by arrangement B10 to kill all the fleas |
|---|---|---|---|---|
| 1 week | 100% | 12 hrs | 100% | 12 hrs |
| 15 days | 100% | 18 hrs | 100% | 18 hrs |
| 1 month | 100% | 20 hrs | 98% | 26 hrs |
| 2 months | 96% | 26 hrs | 91% | 30 hrs |
| 3 months | 89% | 30 hrs | 80% | 36 hrs |
| 4 months | 82% | 36 hrs | 74% | 48 hrs |
| 5 months | 65% | 48 hrs | 59% | 54 hrs |

EFFECTIVENESS ON TICKS

The comparative effectiveness of the two arrangements on ticks is summarised in the following table:

| time since first use | % ticks killed with collar A9 after 24 hours | time taken by arrangement A9 to kill all the ticks | % ticks killed with collar B10 after 24 hours | time taken by arrangement B10 to kill all the ticks |
|---|---|---|---|---|
| 1 week | 100% | 24 hrs | 100% | 24 hrs |
| 15 days | 95% | 32 hrs | 93% | 40 hrs |
| 1 month | 85% | 2 days | 81% | 2½ days |
| 2 months | 78% | 2½ days | 70% | 3½ days |
| 3 months | 65% | 4 days | 58% | 5 days |
| 4 months | 55% | 5 days | 46% | 5% of ticks left after 1 week |

EXAMPLES 11 and 12

Collars for medium sized and large dogs

| All-Composition of collars based on Diazoxone | |
|---|---|
| diazoxone | 15% |
| dioctyl phthalate | 20% |
| magnesium stearate | 2% |
| epichlorophydrin | 3% |
| dye | 0.25% |
| perfume | 0.75% |
| polyvinyl chloride | 59% |

| B12-Composition of Collars based on Diazinone | |
|---|---|
| diazinone | 15% |
| dioctyl phthalate | 20% |
| magnesium stearate | 2% |
| epichlorohydrin | 3% |
| dye | 0.25% |
| perfume | 0.75% |
| polyvinyl chloride | 59% |

C-PREPARATION

The process is performed by moulding or extrusion, as in the preceding cases.

Over a period of 5 months, tests were carried out on large dogs of different breeds infested with fleas and ticks. The animals are subjected to artificial reinfestation every week.

EFFECTIVENESS ON FLEAS

The following table summarises the comparative effectiveness of the two arrangements on fleas.

| time in use | killed with collar A11 after 24 hours | time taken by arrangement A11 to kill all the fleas | % fleas killed with collar B12 after 24 hours | time taken by arrangement B12 to kill all the fleas |
|---|---|---|---|---|
| 1 week | 100% | 12 hrs | 100% | 12 hrs |
| 15 days | 100% | 18 hrs | 100% | 20 hrs |
| 1 month | 100% | 24 hrs | 97% | 26 hrs |
| 2 months | 99% | 26 hrs | 93% | 30 hrs |
| 3 months | 93% | 30 hrs | 85% | 36 hrs |
| 4 months | 86% | 32 hrs | 78% | 48 hrs |
| 5 months | 75% | 48 hrs | 69% | 54 hrs |

EFFECTIVENESS ON TICKS

The effectiveness is summarised in the following table:

| time in use | % ticks killed with collar A11 after 24 hours | time taken by arrangement A11 to kill all the ticks | % ticks killed with collar B12 after 24 hours | time taken by arrangement B13 to kill all the ticks |
|---|---|---|---|---|
| 1 week | 100% | 24 hrs | 100% | 24 hrs |
| 15 days | 93% | 32 hrs | 90% | 40 hrs |
| 1 month | 80% | 2½ days | 75% | 3 days |
| 2 months | 75% | 3 days | 67% | 3½ days |
| 3 months | 67% | 3½ days | 63% | 4 days |
| 4 months | 58% | 4 days | 52% | 5 to 6 days |

These examples show that the effectiveness of the Diazoxone-based collar is greater than that of the Diazinone-based collar.

The invention relates to a composition to protect domestic animals from ectoparasites comprising a mixture of Diazinon and Diazoxon.

Advantageously the composition comprises of from 10 to 90% by weight of Diazinon and of from 90 to 10% by weight of Diazoxon. Better results are obtained when the composition comprises 40–18%, say 60% of Diazinon and 60–20%, say 40% of Diazoxon.

It has been now found that a mixture of Diazinon and Diazoxon is much more effective than each of them taken separately. This permits to reduce the quantity of active ingredient in a collar and thus to reduce the toxicity of the latter. The collar may then be used without danger for young cats (although they are sensitive to organo-phosphorous compounds) and for young dogs.

The synergy of Diazinon with Diazoxon may be explained as it follows:

Diazoxon has a very quick knock down effect. This paralysing and quick effect is not a 100% lethal one. On the contrary the lethal effect of Diazinon is very high, but Diazinon acts much more slowly than Diazoxon.

For instance fleas which continuously move on a dog may cross many times the neck of the dog bearing a Diazinon collar without being killed.

Fleas are paralysed practically immediately as they pass on the neck of a dog bearing a Diazoxon collar. Thus it has been noted that fleas fall down quickly on the white faience ground of a cage where a dog is encaged, said dog bearing a Diazoxon collar. But the fleas are only paralysed. They are not killed. Some of the fleas come back on the dog.

In the case of a collar made with a mixture of Diazinon and Diazoxon, the flea are first paralysed. They stay in the neighbourhood of the collar. This gives time for the lethal Diazinon to act.

The invention relates also to a composition for controling ectoparasites on domestic animals which comprises of from 2–25% of an insecticidal agent and of from 0,5 to 10% of an oil in a matrix of vinylresin.

Insecticidal agents which may be used are carbamates, organo-phosphorous compounds, organo-chlorine compounds, pyrethroids and mixtures thereof.

Carbamates useful in the compositions of the present invention are represented by the formula:

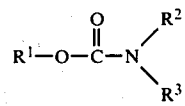

wherein $R^2$ is hydrogen or lower alkyl, $R^3$ is lower alkyl and $R^1$ is aryl, substituted aryl, heterocyclid or substituted heterocyclic groups. The term "lower alkyl," as used herein, refers to an alkyl group, branched or straight chain, having a chain length of one to six carbon atoms. The term "aryl," as used herein, refers to an aryl group such as phenyl or naphthyl. The term "substituted aryl", as used herein, refers to a phenyl or naphthyl group substituted with one or more groups such as lower alkyl, halogen, lower alkoxy, lower alkly-amino, lower dialkylamino or lower alkylthio. The term "heterocyclic," as used herein, refers to a organic cyclic group having an oxygen atom, sulfur atom or nitrogen atom in the nucleus thereof and containing up to 12 carbon atoms. The term "substituted heterocyclic," as used herein, refers to a heterocyclic group substituted with one or more groups such as lower alkyl, lower alkoxy, lower alkylthio, lower alkylamino, lower dialkylamino or halogen.

Typical of the carbamates which can be used in the present invention are
2-isopropylphenyl N-methyl carbamate,
2-isopropoxyphenyl N-methyl carbamate,
3-(1-methylbutyl) phenyl N-methyl carbamate,
3-(1-ethylpropyl) phenyl N-methyl carbamate,
6-chloro-3,4-xylenyl N-methyl carbamate,
4-methylthio-3,5-xylenyl N-methyl carbamate,
1-naphthyl N-methyl carbamate,
1-naphthyl N-ethyl carbamate,
1-naphthyl N-isopropyl carbamate,
1-naphthyl N-butyl carbamate,
1-naphthyl N-hexyl carbamate,
1-(4-chloronaphthyl) N-methyl carbamate,
1-(5,6-dihydronaphthyl) N-methyl carbamate,
1-(5,8-dihydronaphthyl) N-methyl carbamate,
4-benzothienyl N-methyl carbamate,
1-phenyl-3-methylpyrazol-5-yl N,N-dimethyl carbamate, dimethyl carbamate, 2-(N,N-dimethyl carbamyl)-3-methylpyrazol -5-yl N,N-dimethyl carbamate, and mixtures thereof.

The preparation of carbamates of the above formula has been previously described. See, for example, U.S. Pat. Nos. 2,903,478 and 3,203,853.

Some useful alkyl-, alkaryl-, aralkyl- and heterocyclic carbamates, are m-(1 ethylpropyl) phenyl methylcarbamate, m-(1methylbutyl) phenyl methyl carbamate, 2-dimethylamino-5,6-dimethylpyrimidin-4-yl dimethylcarbamate, 4-methylthio-3,5 xylyl-N-methyl carbamate, 2-(1,3-dixolan-2 yl) phenyl-N-methylcarbamate, 3-isopropyl-5-methylphenyl-N-methylcarbamate, 4-dimethylamino-3-tolyl-N methylcarbamate.

Useful organo-phosphorous compounds are phosphoric acid esters of the formula:

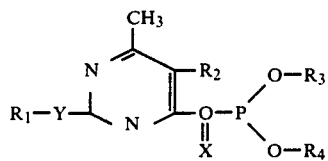

wherein $R_1$ represents a member selected from the group consisting of alkyl, alkenyl, alkoxyalkyl and alkyl-mer-capto-alkyl radicals, $R_2$ represents a member selected from the group consisting of hydrogen, low alkyl and low alkenyl radicals, $R_3$ and $R_4$ represent low alkyl radicals, X represents a member selected from the group consisting of oxygen and sulphur, and Y represents a member selected from the group consisting of the direct link and sulphur.

Specific organo-phosphorous compounds are:
Bromophos
Phoxime
"Phostex"
"Abate"
Iodfenphos
Pyrimiphos
Azidithion
Fenchlorfos
Malathion
Parathion
Azinphos
Butonate
Nichlorfos
Crufomate
Aspon
Chlorothion
Fospirate
"Dursban"
Trichlorphon
Aldimithion
Azothoate
Phosphinon
Mevinphos
Crotoxyphos
Phosphamidon
Birlane
Fenitrothion
Trichlorometaphos
Fenthion
Fensulfothion
Zinophos
Dithion
Endothion
Mercaptophos
Vamidothion
Dimethoate
Formothion
Ethion
Phtalophos
Diazinon II-Pyrethroides Barthrine
Bioresmethrine
Tetrametrine
Resmethrine
Natural Pyrethrines
Allethrine III-Organo-chlorine compounds Bromodan
"Perthane"
Methoxychlore
Morestan
T D E
Pentac
"Dilan"
Chlorfenethol The composition according to the invention comprises 2-25% by weight of the insecticidal agent and more usually 2-15%.

The present composition comprises an oil, that is unsaturated (double bonds) aliphatic hydrocarbon compounds which, in general, has 10-24 carbon atoms, as well as the acid derivates thereof. Some useful oils are codliver oil, linseed oil, poppyseed oil, nut oil, olive oil, maize oil, oleic acid, orange oil, palm kernel oil, rapeseed oil, castor oil, rubsen oil, sesame oil, soya-bean oil, sunflower oil, peanut oil, cotton seed oil, hempseed oil, rosin oil, coconut oil, citronella oil, avocado oil, camphor oil, safflower oil, rape-seed oil, vaseline, mineral oils and mixtures thereof.

The composition comprises 0.5-10% of said oils and more usually 4-8% by weight.

The oil and the insecticidal agent are embedded in a vinylidene or vinylpolymer matrix which is of the same type as the above mentioned macromolecular substance.

It is critical that the double bonds of the oil be still present. Thus epoxydized oil is not appropriate. It has been found that such an oil with double bonds aids the insecticidal agent to entirely migrate from the composition. Thus it is possible to reduce the amount of insecticidal agent and the toxicity of the composition, while obtaining better results for the protection of an animal against ectoparasites. The duration of protection is enhanced. Residual collars contain no more toxic agent.

The following examples illustrate the invention.

EXAMPLE 11

Five collars (C1-C5) are prepared by extruding the compositions as mentioned in the following table.

| Components % | C1 | C2 | C3 | C4 | C5 |
|---|---|---|---|---|---|
| Diazinon | 2 | 4 | 5 | 6 | 8 |
| Diazoxon | 8 | 6 | 5 | 4 | 2 |
| P V C | 62 | 62 | 62 | 62 | 62 |
| Butyl Phthalate | 23 | 23 | 23 | 23 | 23 |
| Epoxydized soya bean oil | 4 | 4 | 4 | 4 | 4 |
| Dye | 0.25 | 0.25 | 0.25 | 0.25 | 0.25 |
| Vanilline | 0.75 | 0.75 | 0.75 | 0.75 | 0.75 |

The results of experiments on dogs which are infested again each week are shown in Table I (see page 34).

It results from table I that the higher effectiveness is obtained for a weight Diazinon/Diazoxon ratio of 3/2.

EXAMPLE 12

Four collars (A1, B1, C6, C7) are prepared as in example 11. They have the compositions mentioned in the following table: (see page 35).

The results of experiments of dogs which are infested again each week are shown in tables II and III (see page 36).

EXAMPLE 13

20 collars E are prepared from:

| components: | weight: |
|---|---|
| Diazinon | 15% |
| P.V.C. | 60% |
| Dibutylphthalate | 20% |
| Epoxydized soya bean oil | 4% |
| Dye | 9.25% |
| Vanilline | 0.75% |

20 collars E 2 were prepared from the same components to which 7% by weight of sesame oil has been added.

Then the cinetic of Diazinon elimination was studied.

The collars were pulled out of their gas-tight bag and were immediately gas-chromatography dosed.

Then they were wiped with a filter-paper and put on a table.

TABLE I

EFFECTIVENESS ON FLEAS

| Time | % fleas or ticks killed with collar C5 after 24 hours | Time taken by C5 to kill all the fleas or ticks | % fleas or ticks killed by C2 after 24 hours | Time taken by C2 to kill all the fleas or ticks | % fleas or ticks killed by C3 after 24 hours | Time taken by C3 to kill all the fleas or ticks | % fleas or ticks killed by C4 after 24 hours | Time taken by C4 to kill all the fleas or ticks | % fleas or ticks killed by C1 after 24 hours | Time taken by C1 to kill all the fleas or ticks |
|---|---|---|---|---|---|---|---|---|---|---|
| 1 week | 100% | 12 h | 100% | 12 h | 100% | 12 h | 100% | 12 h | 100% | 12 h |
| 15 days | 100% | 22 h | 100% | 20 h | 100% | 18 h | 100% | 18 h | 100% | 20 h |
| 1 month | 94% | 26 h | 97% | 26 h | 100% | 22 h | 100% | 20 h | 95% | 26 h |
| 2 months | 85% | 30 h | 89% | 30 h | 95% | 26 h | 100% | 24 h | 88% | 30 h |
| 3 months | 73% | 36 h | 76% | 34 h | 86% | 30 h | 94% | 26 h | 73% | 34 h |
| 4 months | 65% | 42 h | 68% | 40 h | 72% | 34 H | 86% | 30 h | 65% | 40 h |

EFFECTIVENESS ON TICKS

| 1 week | 96% | 30 h | 98% | 26 h | 100% | 22 h | 100% | 20 h | 95% | 30 h |
|---|---|---|---|---|---|---|---|---|---|---|
| 15 days | 90% | 42 h | 92% | 40 h | 93% | 40 h | 96% | 32 h | 89% | 44 h |
| 1 month | 79% | 3.5 days | 81% | 3 days | 84% | 3 days | 88% | 2 days | 75% | 3,5 days |
| 2 months | 67% | 4 days | 70% | 3,5 days | 71% | 3,5 days | 76% | 3 days | 65% | 4 days |
| 3 months | 58% | 5 days | 59% | 4 days | 62% | 4 days | 68% | 3.5 days | 56% | 5 days |
| 4 months | 48% | 6-7 days | 50% | 5-6 days | 54% | 5-6 days | 60% | 4 days | 47% | 1 weeks |

| Components % | Collar A 1 | Collar B 1 | Collar C 6 | Collar C 7 |
|---|---|---|---|---|
| Diazinon | 15% | | 9% | 6% |
| Diazoxon | | 15% | 6% | 4% |
| P V C | 60% | 60% | 60% | 62% |
| Butyl Phthalate | 20% | 20% | 20% | 23% |
| Epoxydized soya bean oil | 4% | 4% | 4% | 4% |
| Dye | 0.25 | 0.25 | 0.25 | 0.25 |
| Vanilline | 0.75 | 0.75 | 0.75 | 0.75 |

TABLE II

| Time after setting in service | % of parasites killed with collar A1 after 24 hours | Time taken by A1 to kill all the parasites | % of parasites killed by B1 after 24 hours | Time taken by B1 to kill all the parasites | % of parasites killed by C6 after 24 hours | Time taken by C6 to kill all the parasites | % of parasites killed by C7 after 24 hours | Time taken by C7 to kill all the parasites |
|---|---|---|---|---|---|---|---|---|
| EFFECTIVENESS ON FLEAS | | | | | | | | |
| 1 week | 100% | 12 h | 100% | 12 h | 100% | 6 h | 100% | 12 h |
| 15 days | 100% | 18 h | 100% | 18 h | 100% | 8 h | 100% | 18 h |
| 1 month | 95% | 26 h | 100% | 20 h | 100% | 12 h | 100% | 20 h |
| 2 months | 90% | 30 h | 94% | 26 h | 100% | 16 h | 100% | 24 h |
| 3 months | 84% | 36 h | 88% | 30 h | 100% | 20 h | 95% | 26 h |
| 4 months | 73% | 48 h | 75% | 34 h | 98% 26 h | 88% | 30 h | |
| 5 months | 60% | 54 h | 62% | 48 h | 93% | 30 h | 74% 36 | |

TABLE III

| Time after setting in service | % of parasites killed with collar A1 after 24 hours | Time taken by A1 to kill all the parasites | % of parasites killed by B1 after 24 hours | Time taken by B1 to kill all the parasites | % of parasites killed by C6 after 24 hours | Time taken by C6 to kill all the parasites | % of parasites killed by C7 after 24 hours | Time taken by C7 to kill all the parasites |
|---|---|---|---|---|---|---|---|---|
| EFFECTIVENESS ON TICKS | | | | | | | | |
| 1 week | 100% | 22 h | 100% | 22 h | 100% | 14 h | 100% | 20 h |
| 15 days | 89% | 40 h | 94% | 32 h | 100% | 20 h | 96% | 32 h |
| 1 month | 76% | 3 days | 82% | 2.5 days | 98% | 26 h | 85% | 2.5 days |
| 2 months | 65% | 3.5 days | 74% | 3 days | 89% | 32 h | 74% | 3 days |
| 3 months | 60% | 4 days | 65% | 3.5 days | 82% | 48 h | 67% | 3.5 days |

TABLE III-continued

| Time after setting in service | % of parasites killed with collar A1 after 24 hours | Time taken by A1 to kill all the parasites | % of parasites killed by B1 after 24 hours | Time taken by B1 to kill all the parasites | % of parasites killed by C6 after 24 hours | Time taken by C6 to kill all the parasites | % of parasites killed by C7 after 24 hours | Time taken by C7 to kill all the parasites |
|---|---|---|---|---|---|---|---|---|
| 4 months | 51% | 5-6 days | 56% | 4 days | 75% | 3 days | 60% | 4 days |

Every evening the collars were carefully wiped to eliminate any Diazinon on the surface. This increases the migration speed of Diazinon. (Under these wiping conditions a collar loses its activity within 3 months).

the collars were dosed for Diazinon each evening immediately after the wiping.

Table A gives the average percent of Diazinon remaining in the 20 conventional tested collars. Graph A shows also the results.

After 11 weeks Diazinon migrated no more out of the collar. The insecticidal agent content remained then constant at about 5%. This figure is also the final dose in any collar used for many months on a dog.

TABLE A

| Time in weeks | 0 | 1 | 2 | 3 | 4 | 5 | 6 | 7 |
|---|---|---|---|---|---|---|---|---|
| % of Diazinon remaining in the collar | 14.95 | 13.12 | 11.98 | 10.91 | 10.03 | 9.24 | 8.51 | 7.85 |
| Time in weeks | 8 | 9 | 10 | 11 | 12 | 13 | 14 | |
| % of Diazinon remaining in the collar | 6.97 | 6.31 | 5.68 | 5.23 | 5.17 | 5.15 | 5.16 | |

TABLE B

| Time in weeks | 0 | 1 | 2 | 3 | 4 | 5 | 6 | 7 | 8 | 9 | 10 |
|---|---|---|---|---|---|---|---|---|---|---|---|
| % of Diazinon remaining in the collar | 15.08 | 12.85 | 11.65 | 10.67 | 9.61 | 8.77 | 7.98 | 7.25 | 6.58 | 5.71 | 5.17 |
| Time in weeks | 11 | 12 | 13 | 14 | 15 | 16 | 17 | 18 | 19 | 20 | 21 |
| % of Diazinon remaining in the collar | 4.42 | 3.85 | 3.28 | 2.70 | 2.21 | 1.76 | 1.31 | 0.84 | 0.67 | 0.56 | 0.55 |

Table B and graph B give the average percent of Diazinon remaining in the collars when 9% of pea-nut oil has been added to the composition for the extrusion of collars.

Diazinon migrated almost entirely from the collars. The collars remain active for 19 weeks.

By the addition of the insaturated oil, all the insecticidal agent is used and the effect is longer.

Other experiments have shown that a collar with 15% by weight of Diazinon and 7% by weight of rapeseed oil is active during 6-7 months. Without any oil, the same collar is active during 4 months.

It is enough to have a 10-12% Diazinon content in a collar where unsaturated oil is present, to obtain a 4 months activity. The overall toxicity of the collar is reduced.

An epoxydized oil did not give the same unexpected results as the above mentioned oils. (See tables A and B).

What we claim is:

1. In an animal collar for controlling fleas and ticks on cats and dogs, a part of said animal collar being formed of a solid vinyl or vinylidene polymer matrix in which is dispersed a pesticidal composition, an improved pesticidal composition consisting essentially of
   (a) 0.5 to 15% by weight of an ethylenically unsaturated oil, and
   (b) a mixture of diethyl 0-(2-isopropyl-4-methyl-6-pyrimidinyl)thionophosphate and diethyl 0-(2-isopropyl-4-methyl-6-pyrimidinyl)phosphate, wherein diethyl 0-(2-isopropyl-4-methyl-6-pyrimidinyl)thionophosphate is 10 to 90% by weight of said mixture and diethyl 0-(2-isopropyl-4-methyl-6-pyrimidinyl)phosphate is 90 to 10% by weight of said mixture.

2. The animal collar of claim 1, wherein each component of said mixture (b) is present in an amount of from 20 to 80% by weight of said mixture.

* * * * *